US008829458B2

(12) United States Patent
Rudolph et al.

(10) Patent No.: US 8,829,458 B2
(45) Date of Patent: Sep. 9, 2014

(54) DEVICE FOR SIMULATING SPECTRAL UV CHARACTERISTIC BY UV LIGHT EMITTING DIODES

(71) Applicant: Atlas Material Testing Technology GmbH, Linsengericht-Altenhasslau (DE)

(72) Inventors: Bernd Rudolph, Alzenau (DE); Mkrtych Khudaverdyan, Schwaebisch Gmuend (DE); Peter March, Frankfurt am Main (DE)

(73) Assignee: Atlas Material Testing Technology GmbH, Linsengericht-Altenhasslau (DE)

( * ) Notice: Subject to any disclaimer, the term of this patent is extended or adjusted under 35 U.S.C. 154(b) by 0 days.

(21) Appl. No.: 13/934,926

(22) Filed: Jul. 3, 2013

(65) Prior Publication Data

US 2014/0027652 A1    Jan. 30, 2014

(30) Foreign Application Priority Data

Jul. 5, 2012    (EP) ...................................... 12175179

(51) Int. Cl.
*G01N 1/44*    (2006.01)
*G01N 17/00*    (2006.01)
(52) U.S. Cl.
CPC ............... *G01N 1/44* (2013.01); *G01N 17/004* (2013.01)
USPC ...................... 250/372; 250/504 R
(58) Field of Classification Search
CPC ......... G01N 7/002; G01N 7/004; F21S 8/006; F21V 9/02; G01J 1/08; G01J 1/429
See application file for complete search history.

(56) References Cited

U.S. PATENT DOCUMENTS

| | | | | | |
|---|---|---|---|---|---|
| 4,931,655 | A | * | 6/1990 | Yoshida et al. | 250/492.1 |
| 5,206,518 | A | * | 4/1993 | Fedor et al. | 250/504 R |
| 5,854,433 | A | * | 12/1998 | Patel et al. | 73/865.6 |
| 5,995,862 | A | * | 11/1999 | Gallorini | 600/407 |
| 6,626,052 | B1 | * | 9/2003 | Martin et al. | 73/865.6 |
| 6,720,562 | B2 | * | 4/2004 | Rathod et al. | 250/395 |
| 6,872,936 | B2 | * | 3/2005 | Rathod et al. | 850/63 |
| 6,946,652 | B2 | * | 9/2005 | Rathod et al. | 250/252.1 |
| 7,038,196 | B2 | * | 5/2006 | Scott et al. | 250/252.1 |
| 7,348,581 | B2 | * | 3/2008 | March et al. | 250/504 R |
| 7,456,416 | B2 | * | 11/2008 | March et al. | 250/504 R |
| 7,544,948 | B2 | * | 6/2009 | Schonlein et al. | 250/372 |

(Continued)

FOREIGN PATENT DOCUMENTS

DE      103 50 020 B3   5/2005
WO      02/12127 A2     2/2002

OTHER PUBLICATIONS

European Search Report mailed Dec. 6, 2012 in corresponding European Application No. 12175179.6.

*Primary Examiner* — David A Vanore
(74) *Attorney, Agent, or Firm* — Staas & Halsey LLP (57) ABSTRACT

In a weathering chamber, a UV radiation device is arranged and at least one sample can be arranged in a sample plane spaced apart from the UV radiation device. The UV radiation device has a plurality of UV light emitting diodes (UV LEDs) containing two or more classes of UV LEDs having different emission bands. The emission bands are chosen in such a way that a spectral distribution with which a specific spectral UV characteristic is approximated can be obtained in the sample plane.

16 Claims, 4 Drawing Sheets

(56) References Cited

U.S. PATENT DOCUMENTS

| | | |
|---|---|---|
| 8,481,982 B2 * | 7/2013 | Johnson et al. ............ 250/493.1 |
| 2004/0075065 A1 | 4/2004 | Spivak |
| 2004/0178367 A1 * | 9/2004 | Fischer et al. ............ 250/504 R |
| 2005/0087768 A1 * | 4/2005 | March et al. ................. 257/200 |
| 2005/0167580 A1 * | 8/2005 | Scott et al. ................. 250/252.1 |
| 2006/0049360 A1 * | 3/2006 | Schoenlein et al. .......... 250/372 |
| 2007/0034026 A1 | 2/2007 | Maciver et al. |
| 2011/0001150 A1 * | 1/2011 | Yu .................................. 257/98 |
| 2011/0037002 A1 * | 2/2011 | Johnson et al. ............ 250/504 R |
| 2011/0108741 A1 * | 5/2011 | Ingram ..................... 250/492.1 |
| 2012/0134131 A1 * | 5/2012 | Nakamura et al. ................ 362/2 |
| 2012/0250297 A1 * | 10/2012 | Higgins ....................... 362/158 |
| 2012/0287668 A1 * | 11/2012 | Richardson et al. .......... 362/602 |
| 2012/0314449 A1 * | 12/2012 | McCollum et al. ........... 362/602 |
| 2013/0294045 A1 * | 11/2013 | Morgenbrod ..................... 362/1 |
| 2014/0008548 A1 * | 1/2014 | Rudolph et al. ......... 250/455.11 |
| 2014/0008551 A1 * | 1/2014 | Rudolph et al. ........... 250/492.1 |

* cited by examiner

DEVICE FOR SIMULATING SPECTRAL UV CHARACTERISTIC BY UV LIGHT EMITTING DIODES

CROSS REFERENCE TO RELATED APPLICATIONS

This application is based on and hereby claims priority to European Patent Application No. 12 175 179.6 filed on Jul. 5, 2012, the contents of which are hereby incorporated by reference.

BACKGROUND

The present invention relates to a device for artificially weathering or testing the lightfastness of samples, to a UV radiation device, and to a method for operating such a device.

In devices for artificial weathering, an assessment of the weather-governed ageing behavior of a sample, in particular of a planar material sample, is carried out, wherein the sample is subjected to artificial weathering. Such devices usually comprise for this purpose a weathering chamber, in which mounting means for the mounting of samples to be weathered and a radiation source for applying radiation, in particular UV radiation, to the samples are arranged.

In such devices for artificially weathering or testing the lightfastness of material samples, the intention usually is to estimate the service life of materials which, in the application thereof, are constantly exposed to natural weather conditions and thus deteriorate under climatic influences such as sunlight, heat from the sun, moisture and the like. In order to obtain a good simulation of the natural weather circumstances, it is advantageous if the spectral energy distribution of the light generated in the device corresponds as much as possible to that of the natural solar radiation, for which reason xenon emitters have been used as radiation source hitherto in such devices. In addition, a time-lapse ageing test of the materials is substantially obtained by the samples being irradiated in a manner greatly intensified relative to the natural conditions, whereby the ageing of the samples is accelerated. Consequently, after a comparatively short time it is possible to make a statement about the long-term ageing behavior of a material sample.

The material samples examined in artificial weathering devices for the most part consist of polymeric materials. In the latter, the weather-governed deterioration is substantially brought about by the UV component of the solar radiation. The photochemical primary processes that take place here, that is to say the absorption of photons and the generation of excited states or free radicals, are temperature-independent. By contrast, the subsequent reaction steps with the polymers or additives can be temperature-dependent, with the result that the observed ageing of the materials is likewise temperature-dependent.

In the weathering test devices known hitherto, a xenon lamp is usually used as radiation source. Although, as is known, the solar spectrum can be simulated very well with this lamp, the emitted radiation has a relatively high spectral component in the infrared spectral range, which has to be suppressed by filters in order to prevent the samples from being heated to an excessively great extent. Moreover, a commercially available xenon radiation source has only a service life of approximately 1500 hours.

Furthermore, a metal halide lamp can also be used as radiation source, but this lamp has the disadvantage that it cannot be regulated, or can be regulated only with great difficulty. The same also applies to fluorescent lamps, which have likewise already been used as radiation sources in weathering test devices and are disadvantageously associated with a relatively short service life.

Furthermore, all the radiation sources mentioned have the disadvantage that they are not spectrally variable.

A further disadvantage of the above-mentioned conventional radiation sources of weathering test devices is that the latter are relatively unwieldy in accordance with their construction and their driving and therefore cannot be adapted for example to changed conditions with regard to the sample surfaces of the material samples to be irradiated.

SUMMARY

Therefore, it is an object of the present invention to configure a UV radiation device within a device for artificial weathering or testing the lightfastness such that with it a spectral UV characteristic can be simulated (or emulated) as well as possible.

This object is achieved by means of the features of the independent patent claims. Advantageous configurations and developments of the invention are specified in the dependent claims and alternative independent claims.

In accordance with a first aspect, the invention relates to a device for artificially weathering or testing the lightfastness of samples, which device comprises a weathering chamber, in which a UV radiation device is arranged. The UV radiation device has a plurality of UV light emitting diodes containing two or more classes of UV LEDs having different emission bands, wherein the emission bands are chosen in such a way that a spectral distribution with which a specific spectral UV characteristic is approximated can be obtained in the sample plane. The UV characteristic to be approximated can be given, for example, by a spectral range of the UV component of natural solar radiation, for example the short-wave rising edge. However, it can also be given by the UV emission band of a known UV light source or else by any other arbitrarily defined spectral UV characteristic.

As is known, light emitting diodes have a virtually monochrome spectral emission characteristic. Accordingly, at least two spectrally different UV LEDs are selected, the emission maximum of which is at different wavelengths. The UV LEDs are preferably selected and arranged and/or driven in such a way that, during operation, without special measures, the desired spectral UV characteristic to be obtained, such as, for instance, the UV component of the solar spectrum, in particular the short wave rising edge thereof, is optimally adapted, to be precise in such a way that the spectral radiation characteristic is sufficiently spatially homogeneous at the sample plane. By way of example, provision can be made for designing the UV radiation device in a simple manner in terms of circuit technology in this respect by virtue of the fact that the UV LEDs are only jointly drivable and are not individually regulatable, if for example the spatial homogeneity of the spectral radiation characteristic that is obtainable during operation meets the requirements. Alternatively, however, provision can also be made for embodying the UV LEDs as individually regulatable. There is thus the possibility of improving the conditions during operation by further measures, for instance by individually regulating the light intensity of the emitted UV radiation by means of the current fed to the LEDs. It is likewise possible to drive the LEDs in electrical pulsed operation, which will be discussed in even greater detail further below.

In accordance with one embodiment, the UV LEDs are arranged in a manner distributed spatially on a planar area in such a way that positionally dependent variations of the spectral distribution in the sample plane lie within predefined limits. In this case, said limits can be predefined in various ways. Firstly, it is possible to predefine a desired spectral distribution which constitutes a best possible approximation assuming, for example, three different classes of UV LEDs having different emission characteristics, it being taken as a basis that the UV LEDs are combined in a point source. A spatial distribution of these UV LEDs is then implemented such that at each point in the sample plane for example the light intensity at each wavelength is permitted to deviate only by a predefined magnitude from the light intensity of the desired spectral distribution at said wavelength and/or at each point in the sample plane a deviation of the light intensities from the light intensities of the desired spectral distribution, which deviation is accumulated over the entire range of the desired spectral distribution, is permitted to deviate only by a predefined magnitude from the accumulated light intensity of the desired spectral distribution.

In accordance with one embodiment, the rising edge of the UV component of natural solar radiation at the short-wave end is approximated with the spectral distribution.

In accordance with one embodiment, the UV emission band of a known UV light source or some other arbitrarily defined spectral UV characteristic is approximated with the spectral distribution.

In accordance with one embodiment, the UV LEDs cannot be driven independently of one another.

In accordance with one embodiment, the UV LEDs can be driven independently of one another. In particular, electric currents having different current intensities can be applied to the UV LEDs or the UV LEDs can be subjected to different time dependencies of the electric currents. It can also be provided that UV LEDs of one class are only jointly drivable, that is to say UV LEDs of one class only emit with a specific predefined light intensity, but UV LEDs of another class can emit jointly with a light intensity different therefrom.

In accordance with one embodiment, the UV LEDs are distributed spatially uniformly. In particular, the UV LEDs are arranged along the rows and columns of a matrix.

In accordance with one embodiment, the number of UV LEDs in the classes having different emission characteristics is different. In accordance with an alternative embodiment, the number of UV LEDs in the classes having different emission characteristics is identical.

In accordance with one embodiment, the UV LEDs are arranged regularly with regard to their association with the classes having different emission characteristics. This can mean e.g. that the UV LEDs are generally arranged along the rows and columns of a matrix and are arranged point-symmetrically with regard to their association with the classes having different emission characteristics. The point symmetry can be configured in such a way that the UV LEDs are arranged point-symmetrically with respect to a specific selected UV LED. This will become even clearer further below in the form of an exemplary embodiment.

In accordance with one embodiment, exactly four classes of UV LEDs having different emission characteristics are provided, which have in particular their maxima at the wavelengths 310 nm, 320 nm, 330 nm and 340 nm.

In accordance with one embodiment, the UV LEDs are mounted on a planar support, such as a circuit board, which can be part of an insert cassette that can be inserted into a cavity provided therefor in the device.

In accordance with another embodiment, the UV LEDs are distributed spatially non-uniformly. This can be configured in such a way that the UV LEDs are arranged in the form of clusters of two, three, four or more UV LEDs, in particular in the form of triples, quadruples or n-tuples (n=natural number). These clusters of UV LEDs can then be distributed, for their part, regularly over the area. By way of example, exactly one UV LED from each class of the classes having different emission characteristics can then be represented within each cluster such as each triple or quadruple. In this respect, too, an exemplary embodiment will be shown further below for more detailed explanation.

In accordance with one embodiment, either the entire UV radiation device or else individual UV LEDs are arranged in a spatially variable manner in relation to one or more samples to be examined. This affords the additional possibility of compensating for or at least reducing spatial inhomogeneities of the spectral distribution of the emitted radiation at the sample plane.

In accordance with one embodiment, a diffusing plate is arranged between the UV radiation device and the sample plane.

In accordance with a second aspect, the invention relates to a UV radiation device comprising a plurality of UV light emitting diodes containing two or more classes of UV LEDs having different emission bands, wherein the emission bands are chosen in such a way that a spectral distribution with which a specific spectral UV characteristic is approximated can be obtained at a distance from the UV radiation device. Such a UV radiation device can be developed with one or more features such as have been described in connection with a device in accordance with the first aspect or such as will be described further below in accordance with the description of the Figures.

In accordance with a third aspect, the invention relates to a method for operating a device in accordance with the first aspect as described above, or a UV radiation device in accordance with the second aspect. This method takes measures to approximate the superimposed emission characteristic of the UV LEDs as well as possible to the spectral UV characteristic to be simulated. These measures include, for example, applying electric currents having different current intensities to the UV LEDs and/or applying electric currents having different time dependencies to the UV LEDs and/or spatially varying or shifting the UV radiation device relative to the sample to be examined.

BRIEF DESCRIPTION OF THE DRAWINGS

The invention is explained in even greater detail below on the basis of exemplary embodiments in conjunction with the Figures of the drawing, in which:

FIGS. 1A, B show examples of spectral UV characteristics to be simulated in the form of a UV rising edge of the solar spectrum (A) and a UV emission characteristic of a UV radiation source (B);

DETAILED DESCRIPTION OF THE PREFERRED EMBODIMENT

FIG. 1A shows the principle underlying the present invention on the basis of a wavelength-intensity diagram. The short-wave rising edge of the UV component of the solar spectrum is illustrated only schematically here as a solid line. Attempts are made to simulate this profile during the weathering test or lightfastness test by means of, for example, three UV LEDs having different emission spectra. The spectra of the three UV LEDs are illustrated as dotted lines, while the superimposed emission spectrum is shown as a dash-dotted line. It likewise already becomes clear from the diagram that the emission spectra are associated with different radiation intensities and the LEDs associated with the emission spectra should therefore have different total radiation intensities. This can be achieved, in principle, in two different ways. Either the number of LEDs contained in the different classes is different, that is to say for example the LEDs associated with the emission spectrum having the longest wavelength are represented to the highest extent numerically, or the number of LEDs contained in the different classes is identical, in which case, however, different current intensities are then applied to the LEDs.

FIG. 1B shows a further wavelength-intensity diagram, in which an exemplary UV emission band of a UV radiation source is shown as a solid line. Its profile can be simulated during the weathering test or lightfastness test by means of, for example, two UV LEDs having different emission spectra, which are depicted in a dotted manner. This results in a superimposed spectrum, depicted in a dash-dotted manner, which represents a good approximation to the spectral UV characteristic to be simulated.

Figure 2:
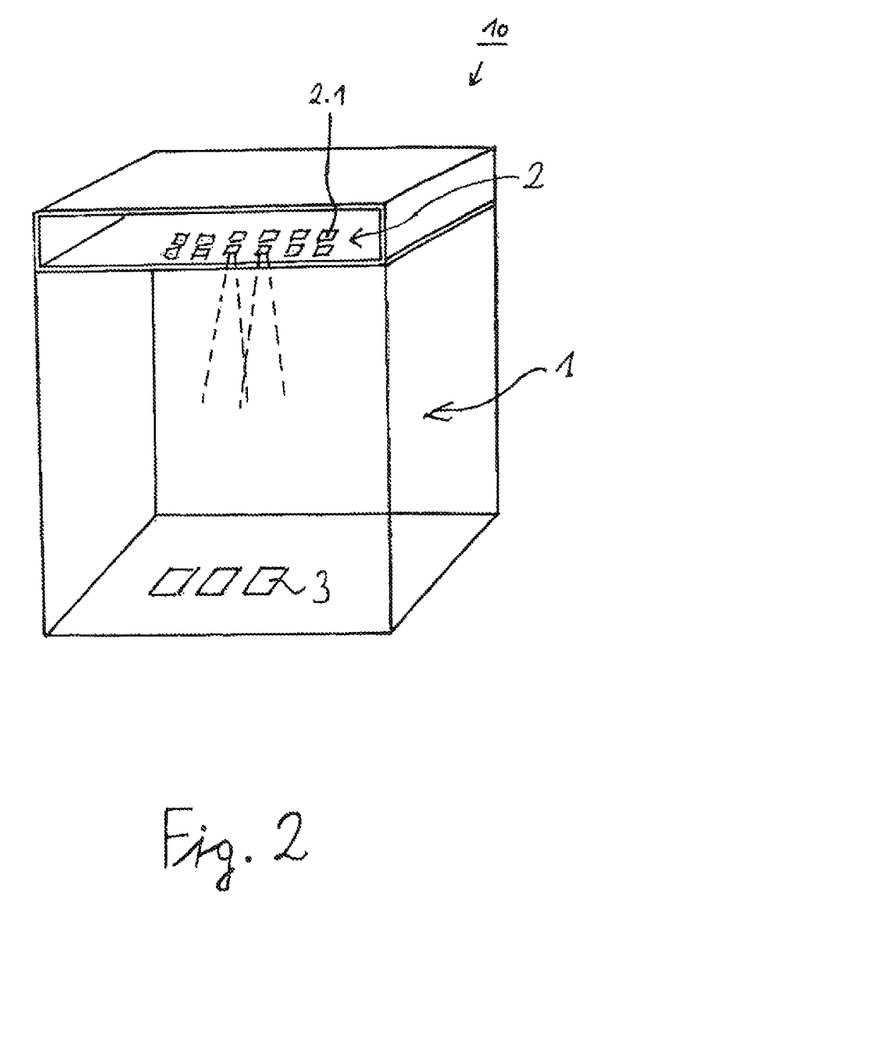
FIG. 2 shows an exemplary embodiment of a device according to the invention for artificially weathering or testing the lightfastness of samples in a perspective view.

FIG. 2 illustrates schematically in perspective view an embodiment for a device for artificial weathering or testing the lightfastness. The device comprises a weathering chamber 1, in which a UV radiation device 2 is arranged. In the lower region of the sample chamber 1, suitable mounting means can be present on a base-plate, a number of samples 3 being able to be mounted by means of said mounting means. The device is therefore designed as a weathering device with stationary sample mounting. However, the invention can likewise be applied to weathering devices comprising movable sample mounts.

The UV radiation device 2 comprises a plurality of UV LEDs 2.1, which can be mounted along the rows and columns of a matrix on a planar area, such as a circuit board, for example, and can be aligned with regard to their emission characteristic in such a way that the emission radiation is directed perpendicularly downward onto the samples 3 to be examined. In one practicable embodiment, the circuit board with the UV LEDs fixed on the lower surface thereof can be provided as part of an insert cassette that can be inserted into a slot provided therefor on the top side of the device 10. In this case, the circuit board can form a lower base area of the insert cassette, while a cooling medium can flow through the spatial region located thereabove, in order to efficiently dissipate the heat generated by the UV LEDs.

It goes without saying that the device 10 can contain further elements which serve for weathering the samples and are not shown here merely for reasons of simplifying the illustration.

Figure 3:
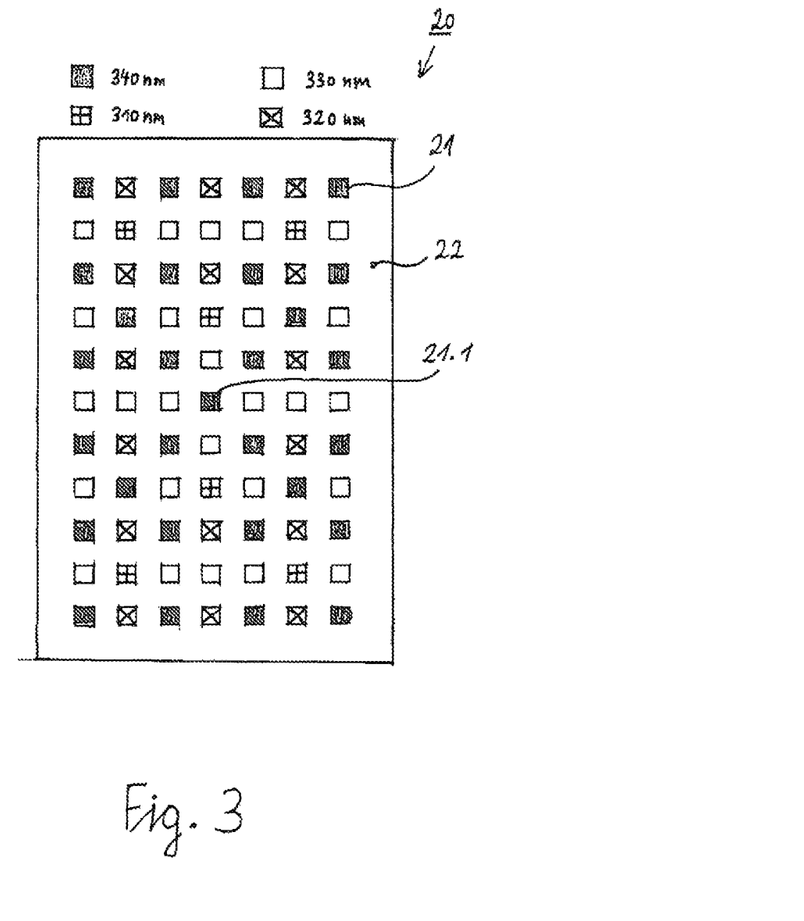
FIG. 3 shows a plan view of a UV radiation device containing a plurality of UV LEDs in accordance with one embodiment.

FIG. 3 shows a plan view of a UV radiation device in accordance with one embodiment. The UV radiation device 20 comprises a plurality of UV LEDs 21, which can be arranged along the rows and columns of a matrix and mounted on a planar support 22 such as a circuit board. The plurality of UV LEDs 21 can contain exactly four classes of UV LEDs 21 having different emission bands. These emission bands can be constituted such that the maxima are at wavelengths of 310 nm, 320 nm, 330 nm and 340 nm.

Figure 1:
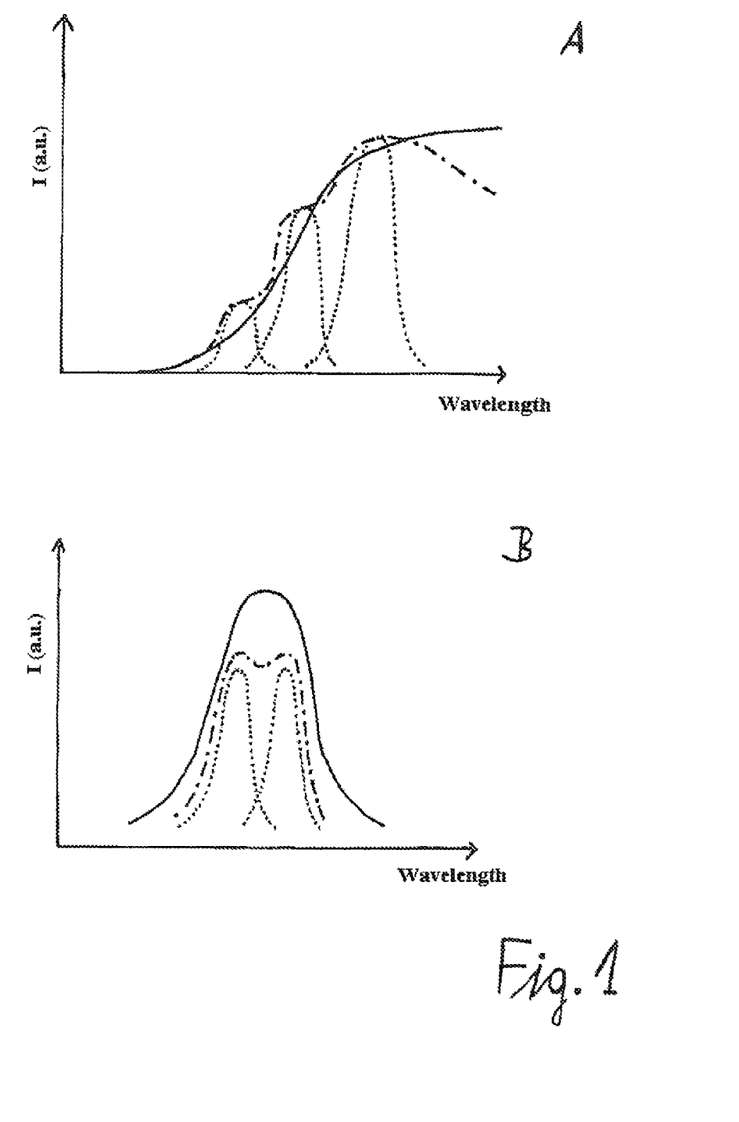

One fundamental problem is that—as shown in FIG. 2—with the UV LEDs distributed over an area, an area which is spaced apart at a distance therefrom and is populated with samples 3 can be irradiated in such a way that with the best possible spatial homogeneity at each point of the area populated with samples 3 a spectral characteristic is provided which simulates the rising edge of the UV component of the solar spectrum, as shown in FIG. 1, or a different spectral UV characteristic. The exemplary embodiment shown in FIG. 3 solves this problem by a specific spatial distribution of the UV LEDs 21 having different emission bands on the planar support 22. Of the total of 77 UV LEDs 21, 29 can have a wavelength maximum at 340 nm, 26 can have a wavelength maximum at 330 nm, 16 can have a wavelength maximum at 320 nm and 6 can have a wavelength maximum at 310 nm. The spatial distribution chosen can then be constituted in such a way that the UV LEDs are arranged regularly in accordance with their emission bands, wherein the regular arrangement can consist in a point symmetry with regard to a central UV LED 21.1. With this spatial arrangement chosen it proves to be possible to obtain a good spatial homogeneity of the spectral distribution of the radiation on a sample area spaced apart therefrom. Other arrangements are also conceivable in this case. Thus, a point-symmetrical arrangement can be chosen, for example, in which the point of symmetry does not consist in a UV LED, but rather is a point located in an interspace between UV LEDs.

An alternative embodiment thereto could consist in the number of LEDs at the four wavelength maxima mentioned being identical, but with different currents being applied to the LEDs. Consequently, a higher current would in each case be applied to the LEDs at 340 nm than to the LEDs at every other wavelength.

Figure 4:
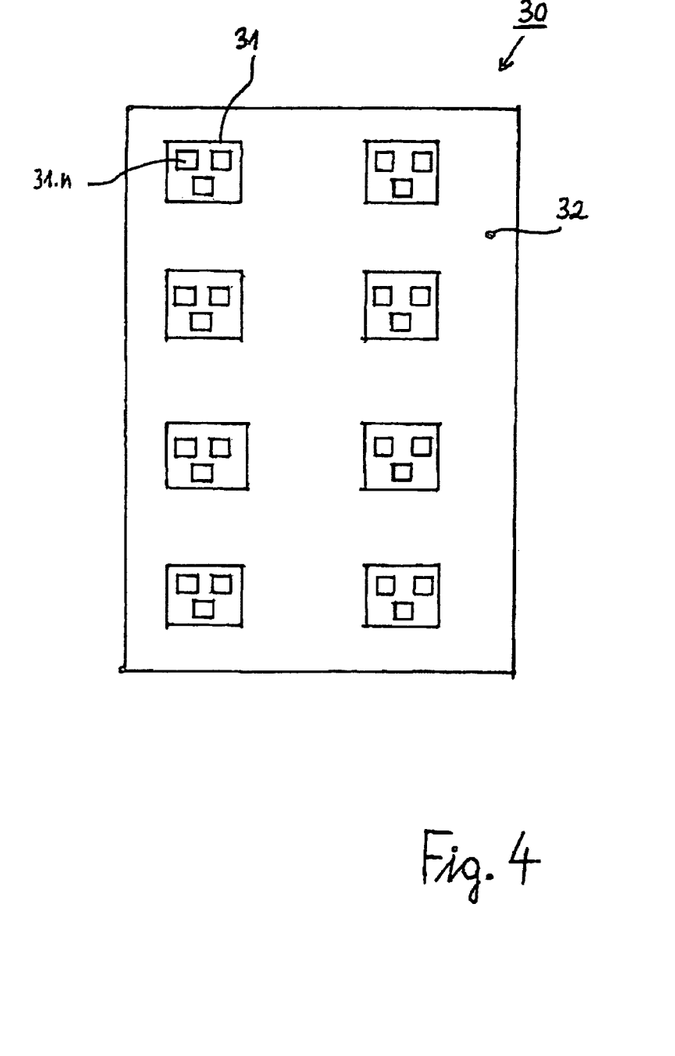
FIG. 4 shows a plan view of a UV radiation device containing a plurality of UV LEDs in accordance with one embodiment.

FIG. 4 shows a plan view of a UV radiation device in accordance with one embodiment. The UV radiation device 30 comprises a plurality of UV LEDs 31.$n$ mounted on a planar support 32 such as a circuit board. In contrast to the arrangement in FIG. 3, the UV LEDs 31.$n$ are not distributed spatially identically, but rather are combined in groups 31, wherein the groups 31 can be formed identically. In the exemplary embodiment illustrated, the groups each contain three UV LEDs 31.$n$ having different UV emission bands, for example UV emission bands such as are illustrated schematically in FIG. 1A, with which the UV rising edge of the solar radiation can be approximated. However, the groups can also contain for example in each case only 2 UV LEDs having emission bands such as are illustrated for example in FIG. 1B. However, each of the groups can also contain more than three UV LEDs having different UV emission bands. If appropriate, UV LEDs of specific classes, that is to say having specific UV emission bands, can also be represented multiply in the groups.

It can furthermore be provided that the UV LEDs 31.$n$ within a group are spaced apart from one another in such a way that the distances are negligible relative to the distance between the UV radiation device 30 and the sample plane. This has the consequence that each group 31 taken by itself generates on the sample plane a spectrum which is mixed ("finished") in the desired manner. The distance between the UV LEDs 31.$n$ can be determined as, for example, an average value of the distances between the midpoints of in each case directly adjacent UV LEDs and this distance can be less than 10 times, 50 times or 100 times the distance between the UV radiation device 30 and the sample plane.

Although specific embodiments have been illustrated and described in this description, it is evident to the person skilled in the art that the specific embodiments shown and described can be exchanged for a variety of alternative and/or equivalent implementations, without departing from the scope of protection of the present invention. This application is intended to cover any adaptations or variations of the specific embodiments discussed herein. It is therefore envisaged that this invention is limited only by the claims and the equivalents thereof.

What is claimed is:

1. A device for artificially weathering or testing the light-fastness of samples, comprising:
    a weathering chamber, in which an ultraviolet radiation device is arranged and at least one sample can be arranged in a sample plane spaced apart from said ultraviolet radiation device,
    wherein the ultraviolet radiation device has a plurality of ultraviolet light emitting diodes containing two or more classes of ultraviolet light emitting diodes having different emission bands,
    wherein the emission bands are chosen in such a way that a spectral distribution with which a specific spectral ultraviolet characteristic is approximated can be obtained in the sample plane, and
    wherein the ultraviolet light emitting diodes of each one of the emission bands are distributed spatially on a planar area in a point-symmetrical arrangement, the symmetry point being defined by one of the ultraviolet light emitting diodes or a point located in an interspace between the ultra-violet light emitting diodes.

2. The device as claimed in claim 1, wherein the ultraviolet light emitting diodes are arranged in a manner distributed spatially on a planar area in such a way that positionally dependent variations of the spectral distribution in the sample plane lie within predefined limits.

3. The device as claimed in claim 1, wherein the rising edge of the ultraviolet component of natural solar radiation at the short-wave end is approximated with the spectral distribution.

4. The device as claimed in claim 1, wherein the ultraviolet emission band of a known ultraviolet light source is approximated with the spectral distribution.

5. The device as claimed in claim 1, wherein the number of ultraviolet light emitting diodes in the classes having different emission bands is different.

6. The device as claimed in claim 1, wherein the number of ultraviolet light emitting diodes in the classes having different emission bands is identical.

7. The device as claimed in claim 1, wherein the ultraviolet light emitting diodes are arranged regularly with regard to their association with the classes having different emission bands.

8. The device as claimed in claim 7, wherein the ultraviolet light emitting diodes are arranged in matrix form and point-symmetrically with regard to their association with the classes having different emission bands.

9. The device as claimed in claim 8, wherein the ultraviolet light emitting diodes are arranged point-symmetrically with respect to a specific selected ultraviolet light emitting diode.

10. The device as claimed in claim 1, wherein the ultraviolet light emitting diodes are distributed spatially non-uniformly.

11. The device as claimed in claim 10, wherein the ultraviolet light emitting diodes are arranged in the form of groups each having two or more ultraviolet light emitting diodes.

12. The device as claimed in claim 1, wherein the ultraviolet light emitting diodes are spatially variable in relation to a sample to be examined.

13. The device as claimed in claim 1, wherein the numbers of ultraviolet light emitting diodes of the emission bands are different from each other.

14. An ultraviolet radiation device, comprising:
    a plurality of ultraviolet light emitting diodes containing two or more classes of ultraviolet light emitting diodes having different emission bands, wherein
    the emission bands are chosen in such a way that a spectral distribution with which a specific spectral ultraviolet characteristic is approximated can be obtained at a distance from the ultraviolet radiation device, and
    the ultraviolet light emitting diodes of each one of the emission bands are distributed spatially on a planar area in a point-symmetrical arrangement, the symmetry point being defined by one of the ultraviolet light emitting diodes or a point located in an interspace between the ultra-violet light emitting diodes.

15. The method as claimed in claim 14, wherein
    electric currents having different current intensities are applied to the ultraviolet light emitting diodes and/or
    the ultraviolet light emitting diodes are subjected to different time dependencies of electric currents and/or
    the ultraviolet light emitting diodes are spatially varied in relation to one or more samples to be examined.

16. A device for artificially weathering or testing the light-fastness of samples, comprising:
    a weathering chamber, in which an ultraviolet radiation device is arranged and at least one sample can be arranged in a sample plane spaced apart from the ultraviolet radiation device, wherein
    the ultraviolet radiation device has a plurality of ultraviolet light emitting diodes containing two or more classes of ultraviolet light emitting diodes having different emission bands,
    the emission bands are provided such that a spectral distribution with which a specific spectral ultraviolet characteristic is approximated can be obtained in the sample plane,
    the ultraviolet light emitting diodes are distributed spatially on a planar area and are arranged in the form of clusters of two, three, four or more ultraviolet light emitting diodes, wherein the clusters are distributed regularly over the area, and
    one ultra-violet light emitting diode from each class of emission bands is represented within each cluster.

* * * * *

UNITED STATES PATENT AND TRADEMARK OFFICE
CERTIFICATE OF CORRECTION

PATENT NO. : 8,829,458 B2  
APPLICATION NO. : 13/934926  
DATED : September 9, 2014  
INVENTOR(S) : Bernd Rudolph et al.

Page 1 of 1

It is certified that error appears in the above-identified patent and that said Letters Patent is hereby corrected as shown below:

In the Claims

Column 8, Line 27, In Claim 15, Delete "method" insert -- device --, therefor.

Signed and Sealed this  
Seventh Day of April, 2015

Michelle K. Lee  
*Director of the United States Patent and Trademark Office*